United States Patent [19]

Sekiguchi et al.

[11] 4,183,867

[45] Jan. 15, 1980

[54] METHOD FOR PREPARATION OF INTERNAL OLEFIN SULFONATE

[75] Inventors: Shizuo Sekiguchi, Funabashi; Katsumasa Nagano, Ichikawa; Kyozo Kitano, Chiba, all of Japan

[73] Assignee: The Lion Fat & Oil Co., Tokyo, Japan

[21] Appl. No.: 930,424

[22] Filed: Aug. 2, 1978

[30] Foreign Application Priority Data

Aug. 25, 1977 [JP] Japan .............................. 52-101905

[51] Int. Cl.$^2$ .......................................... C07C 143/02
[52] U.S. Cl. ................................................. 260/513 T
[58] Field of Search .................................... 260/513 T

[56] References Cited

U.S. PATENT DOCUMENTS 3,428,654  2/1969  Rubinfeld et al. ............... 260/513 T

OTHER PUBLICATIONS

Merck Index, 8th ed., p. 966.

*Primary Examiner*—A. Siegel
*Attorney, Agent, or Firm*—Blanchard, Flynn, Thiel Boutell & Tanis

[57] ABSTRACT

A method of preparing a light-colored internal olefin sulfonate at a high yield, which comprises sulfonating an internal olefin with $SO_3$ gas under 1.3 moles per 1 mole of said olefin thereby producing a sulfonation mixture which still contains 10 to 20% by weight of unreacted olefin, adding anhydrous sodium sulfate and concentrated sulfuric acid to this sulfonation mixture thereby further sulfonating said unreacted olefin, neutralizing the resulting sulfonation product with caustic alkali and then hydrolyzing the thus neutralized product.

5 Claims, No Drawings

METHOD FOR PREPARATION OF INTERNAL OLEFIN SULFONATE

BACKGROUND OF THE INVENTION

The present invention relates to a method of sulfonating an internal olefin, thereby preparing a sulfonate thereof. Particularly it relates to a method of preparing a light-colored internal olefin sulfonate at a high yield. The term "sulfonating", as employed hereinafter in the specification and in the claims, is used sometimes in its generic sense as applying both to true sulfonating and to sulfating, and sometimes in its specific sense, that is, to true sulfonating.

As is generally known, internal olefins are low in reactivity to a sulfonating agent compared with α-olefins. Therefore, on the occasion of sulfonating an internal olefin with $SO_3$ gas, for instance, if a light colored sulfonation product is aimed at, the rate of reaction will markedly lower, and yet, raising of the rate of reaction will extremely deteriorate the color tone of the sulfonation product. Such a tendency is in evidence with respect to α-olefins too. However, in the case of α-olefins, it is possible to obtain a sulfonation product having a light color and containing a low percentage of unreacted olefin by adoption of the so-called two step-sulfonation process which comprises conducting sulfonation with $SO_3$ gas under relatively mild conditions and subsequently conducting sulfonation with concentrated sulfuric acid. But, in the case where this two step-sulfonation process is applied to an internal olefin, because of the poor reactivity of the internal olefin per se, the sulfonation mixture obtained through the former step of sulfonation is still rich in unreacted olefin and there is brought about a situation that this unreacted olefin would get polymerized in the course of the latter step of sulfonation, thereby rendering it impossible to obtain the desired sulfonation product at a high yield.

The present inventors have made a series of studies with a view to settling the foregoing problems peculiar to internal olefins and have come to a finding that on the occasion of effecting sulfonation of an internal olefin through the two step sulfonation process, it is possible to prepare a light-colored internal olefin sulfonate at a high yield when the former step of sulfonation is performed by applying a relatively high ratio of $SO_3$ to the olefin and the latter step of sulfonation is performed in the presence of anhydrous sodium sulfate.

The art of effecting sulfonation reaction in the presence of some inorganic sulfate like sodium sulfate as such has been introduced through the specification for U.S. Pat. No. 4,021,406 disclosing a process for manufacturing sulfo-fatty acid esters. But, the object of the use of inorganic sulfates in this prior art is to prevent the cleavage of ester bond and concurrently avoid the degeneration of color tone of the product. That is, this prior art has no ideas of preventing the polymerization of unreacted olefins by adding inorganic sulfates thereto.

SUMMARY OF THE INVENTION

The method of the present invention comprises: (a) sulfonating an internal olefin with $SO_3$ gas under 1.3 moles per 1 mole of said olefin, thereby producing a first sulfonation mixture which still contains 10 to 20% by weight of unreacted olefin, (b) further sulfonating said unreacted olefin by adding anhydrous sodium sulfate and concentrated sulfuric acid to this first sulfonation mixture, and (c) neutralizing the resulting second sulfonation mixture with caustic alkali and hydrolyzing thereafter.

As the starting material olefin in the present invention, an internal olefin having 10 to 22 carbon atoms is used. In the first sulfonation process employing $SO_3$ gas according to the present invention, a falling film type reactor and a vessel type reactor are both useful, and as to the conditions for sulfonation, the conventional conditions for sulfonation are applicable save for modification of the mole ratio of $SO_3$ to olefin to be under 1.3, generally to be in the range of from 1.0 or more to under 1.3. However, it goes without saying that, inasmuch as the content of unreacted olefin in the first sulfonation mixture obtained through this first sulfonation process is required to be in the range of from 10 to 20% by weight, the temperature for reaction, the time for contact, etc. should be properly selected, taking the foregoing mole ratio into consideration.

The second sulfonation process of the present invention is a process for effecting sulfonation of the first sulfonation mixture obtained through the first sulfonation process with concentrated sulfuric acid of 90% or more in concentration in the presence of a powdery anhydrous sodium sulfate. This process is preferably performed by the use of a vessel type reactor. The amount of said anhydrous sodium sulfate and that of concentrated sulfuric acid to be applied are in the range of from 1 to 20 parts by weight for the anhydrous sodium sulfate and in the range of from 10 to 50 parts by weight for the concentrated sulfuric acid per 100 parts by weight of the first sulfonation mixture obtained from the first sulfonation process. When the anhydrous sodium sulfate and concentrated sulfuric acid in a predetermined amount respectively are added to the sulfonation mixture obtained from the first process and thereafter the mixture is stirred for 10 to 60 minutes while maintaining the temperature of the reactant at 30° C. or less, the remaining unreacted olefin is sulfonated with said concentrated sulfuric acid without being substantially polymerized, and there can be finally obtained a sulfonation product having a sulfonation degree exceeding 90%.

The second sulfonation mixture obtained from the second sulfonation process is next neutralized with caustic alkali by the conventional method, is hydrolyzed thereafter, and becomes an internal olefin sulfonate.

As will be understood from the foregoing elucidation, according to the method of the present invention, on the occasion of performing sulfonation of an internal olefin having a poor reactivity through the two step-sulfonation process, in the first sulfonation process, said internal olefin is sulfonated as much as possible within the range not accompanying any substantial deterioration of the color tone with $SO_3$ gas, and in the second sulfonation process unreacted olefin is sulfonated with concentrated sulfuric acid while polymerization of said unreacted olefin is checked by anhydrous sodium sulfate, and therefore, by treating the sulfonation product obtained through both processes with caustic alkali, there can be obtained a light-colored internal olefin sulfonate at a high yield.

DESCRIPTION OF THE PREFERRED EMBODIMENTS

EXAMPLE

By subjecting an internal olefin having 16 to 18 carbon atoms to sulfonation with $SO_3$-containing gas (concentration of $SO_3$: 1.5% by volume) by means of a falling film type reactor having the inside diameter of 6 mm$\phi$ and length of 1.2 m as made of glass under the conditions of 50° C. in temperature and 1.05 in mole ratio of $SO_3$ to olefin, there was obtained a sulfonation mixture [A]. Next, after putting this sulfonation mixture [A] in a 300 ml Erlenmeyer flask, anhydrous sodium sulfate equivalent to 5% by weight of the sulfonation mixture together with 95% sulfuric acid equivalent to 20% by weight of the same were added thereto, and stirring was conducted for 30 minutes at a temperature of 30° C. Then, the resulting reaction mixture was neutralized with a 10% aqueous solution of NaOH. Subsequently, the thus neutralized mixture was transferred to a 1 l autoclave and subjected to hydrolysis with 30 minutes' stirring at a temperature of 140° C., whereby there was obtained a final sulfonation product. This example is hereunder referred to as Experiment No. 1.

Next, a series of experiments, whose substance is the same as that of Experiment No. 1 except for varying the mole ratio of $SO_3$ to olefin, were conducted.

When the amount of unreacted oil in the sulfonation mixture [A] and in the final product and the color tone of the final product in each experiment were measured by the following methods, the results were as shown in the following table.

Measurement of the amount of unreacted oil contained in sulfonation mixture [A]

By putting 10 g of the sulfonation mixture [A], 300 ml of ethylene glycol and 30 ml of a 48% aqueous solution of NaOH in a 2 l flask with round bottom and effecting azeotropic distillation at a liquid temperature of 180° to 190° C. for 30 minutes, estimation of the unreacted oil content was conducted.

Measurement of the amount of unreacted oil contained in final product

Normal hexane extraction method was adopted.

Measurement of the color tone of final product

After diluting the final product into a concentration of 5% with water, measurement of $(-\log T) \times 10^3$ was conducted by means of an spectrophotometer manufactured by HITACHI SEISAKUSHO, Ltd. under the conditions of 0.05 mm in width of slit and 240 m$\mu$ in wavelength.

| Experiment No. | Mole ratio $SO_3$ to olefin | Unreacted oil content in sulfonation mixture [A] (%) | Final product Unreacted oil content (%) | Color tone |
|---|---|---|---|---|
| 1 | 1.05 | 18.1 | 9.0 | 160 |
| 2 | 1.1 | 16.5 | 7.5 | 350 |
| 3 | 1.20 | 11.0 | 5.5 | 700 |
| 4 | 1.27 | 10.5 | 4.0 | 820 |
| 5* | 1.20 | 11.0 | 8.5 | 650 |
| 6* | 1.27 | 11.0 | 6.5 | 870 |
| 7* | 1.05 | 18.1 | 11.0 | 140 |
| 8* | 1.2 | — | 10.7 | 680 |

(Remark)
Mark *signifies comparative experiment wherein the sulfonation mixture [A] was sulfonated with concentrated sulfuric acid in the absence of anhydrous sodium sulfate, and the amount of said concentrated sulfuric acid applied was identical in Experiment Nos. 1 through 4. But Experiment No. 8 represents on example wherein the sulfonation mixture [A] was directly treated with alkali.

As is evident from comparison of the results of Experiment Nos. 1 through 4 with the results of Experiment Nos. 5 through 7, according to the method of the present invention, it is possible to manufacture a light-colored internal olefin sulfonate at a high yield, that is, in the state of containing unreacted olefin in small quantities.

What is claimed is:

1. The method for preparing internal olefin sulfonates which comprises:
   (a) sulfonating an internal olefin with $SO_3$ gas at a molar ratio of less than 1.3 moles of $SO_3$ per 1 mole of said internal olefin, under conditions effective to produce a first sulfonation reaction mixture which contains from 10 to 20% by weight of unreacted internal olefin;
   (b) adding anhydrous sodium sulfate and concentrated sulfuric acid having a concentration of 90% or more to said first sulfonation reaction mixture, under conditions effective to sulfonate said unreacted internal olefin to produce a second sulfonation reaction mixture, the amount of said anhydrous sodium sulfate being effective to minimize polymerization of said unreacted internal olefin; and
   (c) neutralizing the thus-obtained second sulfonation reaction mixture with caustic alkali and hydrolyzing it thereafter.

2. A method according to claim 1, wherein the starting material is an internal olefin having 10 to 22 carbon atoms.

3. A method according to claim 1, wherein step (b) is performed at a temperature of 30° C. or less for 10 to 60 minutes by adding from 1 to 20 parts by weight of anhydrous sodium sulfate and from 10 to 50 parts by weight of sulfuric acid per 100 parts by weight of said first sulfonation reaction mixture.

4. The method for preparing internal olefin sulfonates which consists essentially of the steps of:
   (a) sulfonating an internal olefin having from 10 to 22 carbon atoms with $SO_3$ gas, at a molar ratio of from 1.0 to less than 1.3 moles of $SO_3$ per one mole of said internal olefin, under conditions effective to produce a first sulfonation reaction mixture containing from 10 to 20% by weight of unreacted internal olefin;
   (b) then adding to 100 parts by weight of said first sulfonation reaction mixture (1) from 1 to 20 parts by weight of anhydrous sodium sulfate powder and (2) from 10 to 50 parts by weight of concentrated sulfuric acid having a concentration of 90% or more, and stirring the mixture for 10 to 60 minutes, at a temperature of 30° C. or less, to sulfonate the unreacted internal olefin while preventing substantial polymerization thereof whereby to obtain a second sulfonation reaction mixture; and
   (c) then neutralizing said second sulfonation reaction mixture with caustic alkali and then hydrolyzing the neutralized second sulfonation reaction mixture, whereby to obtain a light-colored internal olefin sulfonate at a high yield.

5. The method of claim 4 in which said caustic alkali is an aqueous solution of NaOH.

* * * * *